US008647330B2

(12) United States Patent
Iida

(10) Patent No.: US 8,647,330 B2
(45) Date of Patent: Feb. 11, 2014

(54) MANIPULATOR JOINT DISPLACEMENT DETECTION MECHANISM

(75) Inventor: Masatoshi Iida, Hachioji (JP)

(73) Assignee: Olympus Corporation, Tokyo (JP)

( * ) Notice: Subject to any disclaimer, the term of this patent is extended or adjusted under 35 U.S.C. 154(b) by 998 days.

(21) Appl. No.: 12/726,671

(22) Filed: Mar. 18, 2010

(65) Prior Publication Data
US 2010/0241135 A1  Sep. 23, 2010

(30) Foreign Application Priority Data

Mar. 19, 2009 (JP) .................................. 2009-069059

(51) Int. Cl.
*A61B 17/00* (2006.01)
(52) U.S. Cl.
USPC ............................................. 606/1; 606/130
(58) Field of Classification Search
USPC ............. 606/1, 53, 79, 87, 88, 130, 138, 139; 600/101, 104, 114, 117, 118, 127, 129, 600/137; 74/490.01, 490.04–490.09
See application file for complete search history.

(56) References Cited

U.S. PATENT DOCUMENTS

| | | | |
|---|---|---|---|
| 5,339,799 A * | 8/1994 | Kami et al. ..................... 600/117 |
| 5,807,377 A * | 9/1998 | Madhani et al. .................. 606/1 |
| 7,744,622 B2 * | 6/2010 | Brock et al. ................... 606/205 |
| 7,918,861 B2 * | 4/2011 | Brock et al. ................... 606/130 |
| 8,375,808 B2 * | 2/2013 | Blumenkranz et al. .. 73/862.044 |
| 2009/0105726 A1 * | 4/2009 | Sugiyama ...................... 606/130 |

FOREIGN PATENT DOCUMENTS

| | | |
|---|---|---|
| JP | 2000-279376 A | 10/2000 |
| JP | 2002-264048 A | 9/2002 |
| JP | 2003-265499 A | 9/2003 |
| JP | 2008-543590 A | 12/2008 |

OTHER PUBLICATIONS

English-language abstract of International Publication No. WO 2006/136827.

Japanese Office Action dated Apr. 16, 2013 from corresponding Japanese Patent Application No. 2009-069059 together with an English language translation.

* cited by examiner

*Primary Examiner* — Ahmed Farah
(74) *Attorney, Agent, or Firm* — Scully, Scott, Murphy & Presser, P.C.

(57) ABSTRACT

A manipulator joint displacement detection mechanism includes a manipulator which has a actuating unit and a joint. A first transmission member is connected to the joint, and provided movably to displace the joint. A second transmission member moves corresponding to movement of the first transmission member. A guide guides movement of the second transmission member. A guide fixing part fixes one end and the other end of the guide. A sensor detects a moving distance of the second transmission member in the proximal end portion of the manipulator.

20 Claims, 1 Drawing Sheet

MANIPULATOR JOINT DISPLACEMENT DETECTION MECHANISM

CROSS-REFERENCE TO RELATED APPLICATIONS

This application is based upon and claims the benefit of priority from prior Japanese Patent Application No. 2009-069059, filed Mar. 19, 2009, the entire contents of which are incorporated herein by reference.

BACKGROUND OF THE INVENTION

1. Field of the Invention

The present invention relates to a medical manipulator used for laparoscopic surgery, for example, and in particular to a manipulator joint displacement detection mechanism for detecting the degree of displacement of a joint of a manipulator.

2. Description of the Related Art

A medical manipulator is used for laparoscopic or thoracoscopic surgery. The medical manipulator is provided with a joint in the distal end portion. A joint is provided with a clutching unit equipped with a surgical instrument such as a pair of forceps. The medical manipulator transmits power of a driving source such as a motor to a joint. A member to transmit power (power transmission member) is a linear member such as a wire. A power transmission member is provided movably along a guide member inserted in the medical manipulator. A joint is displaced by the transmitted power. A clutching unit changes an angle of rotation of the pair of forceps, for example, according to displacement of a joint.

In laparoscopic or thoracoscopic surgery, a patient's abdomen is punctured, and a jig called a trocar is inserted into the puncture. A medical manipulator equipped with a surgical instrument at the distal end is inserted into the patient's abdomen through the insertion hole of the trocar. In this state, the surgical instrument of the medical manipulator is operated, and surgery is performed.

The aperture of an insertion hole of a trocar used at present is less than 10 mm in diameter. The aperture of the medical manipulator inserted into the trocar must be smaller than the aperture of the trocar. A typical medical manipulator is used in the Intuitive Surgical Corporation's Da Vinci system. The medical manipulator used in this system is formed to have a diameter of 10 mm or less, and a length of 300 mm or greater, in which a clutching unit equipped with a surgical instrument such as a pair of forceps is operated with multiple degrees of freedom.

A power transmission member of the medical manipulator uses a linear member such as a wire. Even the manipulator of the Da Vinci system uses a power transmission member such as a wire. The power transmission member is formed to have a diameter of less than 0.5 mm, for example, to transmit power in a limited space of diameter less than 10 mm.

A manipulator using a linear power transmission member having a small diameter is disclosed in U.S. Pat. No. 5,807,377, for example. This patent application discloses a technique of detecting displacement of a joint by a potentiometer or encoder placed close to a driving source such as a motor.

BRIEF SUMMARY OF THE INVENTION

According to an aspect of the invention, a manipulator joint displacement detection mechanism comprises a manipulator which includes a actuating unit and a joint, and is formed in an elongated shape having a distal end portion and a proximal end portion, the actuating unit provided in the distal end portion, and the joint configured to displace to perform an actuating operation to the actuating unit, and transmit the displacement to the actuating unit to perform the actuating operation; a first transmission member which is connected to the joint, and provided movably to displace the joint; a second transmission member which is connected to the first transmission member in a part of the manipulator close to the joint, and is moved corresponding to a moving distance of the first transmission member; a guide which guides the movement of the second transmission member; a sensor which detects the moving distance of the second transmission member in a part close to the proximal end portion of the manipulator; a joint holder which holds the joint; a sensor holder which holds the sensor; a first guide fixing part which is provided in the joint holder, and fixes one end of the guide; and a second guide fixing part which is provided in the sensor holder, and fixes the other end of the guide.

DETAILED DESCRIPTION OF THE INVENTION

Figure 1:
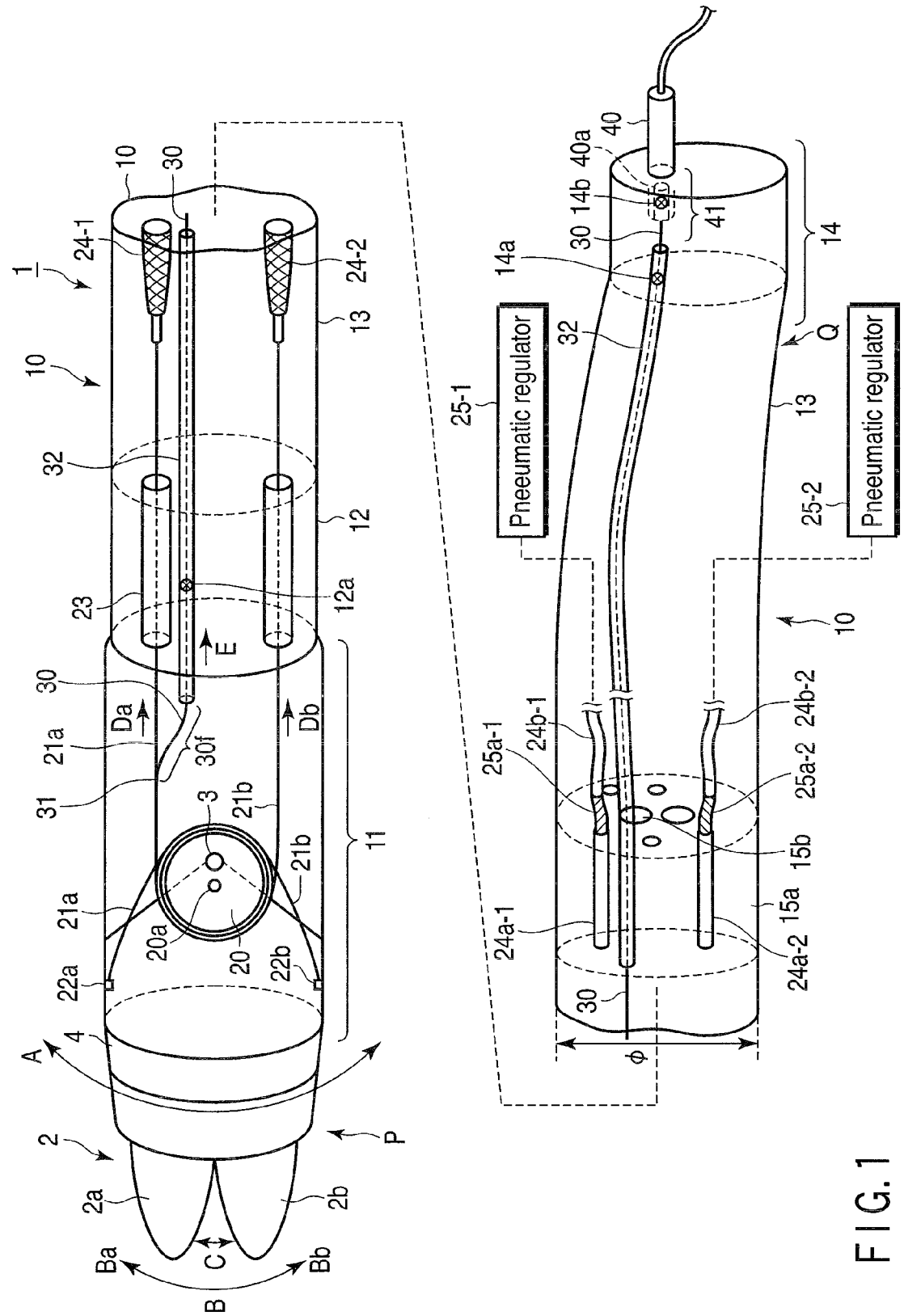
FIG. 1 is a diagrammatic illustration of an embodiment of a displacement detection mechanism of a manipulator joint according to the invention.

Hereinafter, an embodiment of the invention will be explained with reference to the accompanying drawing.

FIG. 1 shows a configuration of a displacement detection mechanism of a medical manipulator joint. A medical manipulator (manipulator) 1 is formed to have an elongated cylindrical shape. The manipulator includes a housing 10, a joint 4, and an actuating unit 2.

The actuating unit 2 is provided in a distal end portion P of the manipulator 1. The actuating unit 2 actuated with motion of the joint 4. The actuating unit 2 is a clutching unit 2 such as a pair of forceps. The clutching unit 2 includes claws 2a and 2b. The clutching unit clutches a diseased part by opening and closing the claws 2a and 2b. The clutching unit 2 is operated with three degrees of freedom, for example. The clutching unit 2 is rotatably fixed to an axis 3. The axis 3 is operated with one of three degrees of freedom. Operation with three degrees of freedom consists of rotation of the clutching unit 2 in the direction of arrow A about the central axis of the manipulator 1, oscillation of the clutching unit 2 in the direction of arrow B about the axis 3, and clutching by opening and closing of the claws 2a and 2b of the clutching unit 2 in the direction of arrow C. One joint 4 is provided for one degree of freedom. When the clutching unit 2 has three degrees of freedom, three joints 4 are provided.

In FIG. 1, the manipulator 1 has one degree of freedom, that is, oscillation, to simplify the explanation. The housing 10 is elongated and cylindrical, and has a diameter of 10 mm, for example. The housing 10 comprises a joint holder 11, a joint holder side guide holder (joint-side guide holder) 12, a cylindrical unit 13, and a sensor holder 14, which are provided in the cylindrical interior.

The joint 4 is provided in the distal end portion of the housing 10. The clutching unit 2 is provided at the distal end of the joint 4. The joint 4 causes the clutching unit 2 to oscillate when displaced.

The joint holder 11 holds the joint 4. The joint holder 11 is made of material such as SUS.

The cylindrical unit 13 is provided in the proximal end portion Q of the joint-side guide holder 12. The cylindrical unit 13 may be made of flexible or semi-flexible material.

The manipulator 1 is integrally composed of the clutching unit 2, the joint 4, the joint holder 11, the joint-side guide holder 12, the cylindrical unit 13, and the sensor holder 14, from the distal end portion P to the proximal end portion Q.

A pair of pulleys 20 is rotatably provided in the joint holder 11. The pulleys 20 are provided in parallel on the same axis of rotation. Two power transmission wires (first and second power wires) 21a and 21b are looped over the pulleys 20. The first and second power wires 21a and 21b are required to operate with one degree of freedom. The first and second power wires 21a and 21b are wound once around the pulleys 20. The first and second power wires 21a and 21b are made of material such as SUS.

One end of the first power wire 21a is fixed to the fixing part 22a in the joint holder 11. One end of the second power wire 21b is fixed to the fixing part 22b in the joint holder 11. The fixing parts 22a and 22b are provided behind the joint 4.

The first and second power wires 21a and 21b are extended longitudinally in the housing 10. The first and the second power wires 21a and 21b are movable axially (linear direction) in the housing 10.

When the first power wire 21a is moved axially, as indicated by arrow Da, the joint 4 is pulled toward the proximal end Q of the manipulator 1. When the first power wire 21a is moved in the reverse direction to arrow Da, the joint 4 is pushed to the distal end P of the manipulator 1.

When the second power wire 21b is moved axially, as indicated by arrow Db, the joint 4 is pulled toward the proximal end Q of the manipulator 1. When the second power wire 21b is moved in the reverse direction to arrow Db, the joint 4 is pushed to the distal end P of the manipulator 1.

When the first power wire 21a is moved axially, as indicated by arrow Da, the clutching unit 2 is caused to oscillate in the direction of arrow Ba. When the second power wire 21b is moved axially, as indicated by arrow Db, the clutching unit 2 is caused to oscillate in the direction of arrow Bb.

The joint-side guide holder 12 connects the joint holder 11 and cylindrical unit 13. A power guide 23 is provided in the joint-side guide holder 12. The power guide 23 is formed a hole in the joint-side guide holder 12. In the power guide 23, a first power wire 21a is movably inserted, and guides movement of the first power wire 21a axially (in the direction of arrow Da and the reverse direction).

If the clutching unit 2 is operated with three degrees of freedom, two power transmission wires needed. Six power guides 23 are provided in the joint-side guide holder 12. Six power guides 23 are provided with equal intervals on the circumference of a predetermined radius of the joint-side guide holder 12 along the longitudinal axis.

The cylindrical unit 13 connects the joint-side guide holder 12 and sensor holder 14. The cylindrical unit 13 is formed as a cylinder.

A sensing wire guide 32 is inserted into the housing 10. The sensing wire guide 32 is made of a tubular member, specifically a hollow tube. Hereinafter, the sensing wire guide 32 is called a sensing guide tube. The sensing guide tube 32 is provided in the joint holder 11, the cylindrical unit 13, and the sensor holder 14. In the sensing guide tube 32, a displacement sensing wire (sensing wire) 30 is movably inverted axially. The sensing guide tube 32 guides movement of the sensing wire 30. The sensing wire 30 is moved along its own axis (linearly in the direction of arrow E and the reverse direction).

The sensing guide tube 32 has a diameter a little larger than the diameter of the sensing wire 30. The outside diameter of the sensing guide tube 32 is 0.5 mm or less, for example. The sensing guide tube 32 is made of material to reduce friction with the sensing wire 30. The sensing guide tube 32 is made of SUS, for example. The inside wall of the sensing guide tube 32 is polished to reduce friction with the sensing wire 30.

One end of the sensing wire 30 is connected to the first power wire 21a. The sensing wire 30 transmits a moving distance of the first power wire 21a. A part connecting the sensing wire 30 and the first power wire 21a is called a connecting part 31. The connecting part 31 is located close to the joint 4 in the sensing wire 30. The sensing wire 30 and the first power wire 21a are connected by soldering or bonding. The connecting part 31 may be formed by connecting the first power wire 21a to one end of the sensing wire 30 with a clip-shaped member. The sensing wire 30 and the first power wire 21a may be connected by providing a resin connecting member with a hole, inserting the sensing wire 30 and the first power wire 21a into the hole, and heating the sensing wire 30 and the first power wire 21a.

The sensing wire 30 is made of magnetic material, such as SUS. The sensing wire 30 is formed as a thin linear wire having a diameter less than that of the first power wire 21a. One sensing wire 30 is connected to one first power wire 21a. If the clutching unit has three degrees of freedom, six sensing wires 30 are provided in the housing 10.

The sensing wire 30 and the first power wire 21a are provided in parallel close to each other. The power guide 23 and the sensing guide tube 32 are provided in parallel close to each other. If the clutching unit 2 has three degrees of freedom, six tubular power guides 23 and six sensing guide tubes 32 are provided. The power guide 23 and sensing guide tube 32, in which the connected first power wire 21a and sensing wire 30 are inserted, are provided in parallel close to each other.

The sensing wire 30 is exposed from the sensing guide tube 32 in the part between the connecting part 31 and one end of the sensing guide tube 32. The exposed part of the sensing wire 30 is called a first wire exposed part 30f.

First and second pneumatic actuators 24-1 and 24-2 are provided in the cylindrical unit 13. The first and second pneumatic actuators 24-1 and 24-2 constitute a driving source for causing the clutching unit 2 to oscillate, for example.

The first pneumatic actuator 24-1 is held by an actuator holder 15a in the cylindrical unit 13. One end of the first pneumatic actuator 24-1 is connected to the first power wire 21a, and the other end of the first pneumatic actuator 24-1 is connected to a pneumatic regulator 25-1 through an actuator fluid inlet/outlet 25a-1 and an actuator tube 24b-1.

The fluid inlet/outlet 25a-1 is formed long enough to be inserted into the actuator holder 15a. The fluid inlet/outlet 25a-1 is shaped like a pipe, for example. The fluid inlet/outlet 25a-1 is inserted into an actuator fixing hole 24a-1. The first pneumatic actuator 24-1 is held in the actuator holder 15a by the fluid inlet/outlet 25a-1.

The actuator holder 15a is provided with an actuator holder guide through-hole 15b. The sensing guide tube 32 is inserted in the actuator holder through-hole 15b.

The first pneumatic regulator 25-1 controls the pneumatic pressure of the first pneumatic actuator 24-1. The first pneumatic actuator 24-1 is expanded and contracted by the pneumatic pressure control. The first pneumatic actuator 24-1 contracts and moves the first power wire 21a axially, as indicated by arrow Da, and expands and moves the first power wire 21a in the reverse direction to arrow Da.

One end of the second pneumatic actuator 24-2 is connected to the second power wire 21b. The other end of the second pneumatic actuator 24-2 is connected to a pneumatic regulator 25-2 through an actuator fluid inlet/outlet 25a-2 and actuator tube 24b-2.

The fluid inlet/outlet 25a-2 is formed long enough to be inserted into the actuator holder 15a. The fluid inlet/outlet 25a-2 is shaped like a pipe, for example. The fluid inlet/outlet 25a-2 is inserted into an actuator fixing hole 24a-2. The second pneumatic actuator 24-2 is held in the actuator holder 15a by the fluid inlet/outlet 25a-2.

The second pneumatic regulator 25-2 controls the pneumatic pressure of the second pneumatic actuator 24-2. The second pneumatic actuator 24-2 is expanded and contracted by the pneumatic pressure control. The second pneumatic actuator 24-2 contracts and moves the second power wire 21b axially, as indicated by arrow Db, and expands and moves the second power wire 21b in the reverse direction to arrow Db.

One of the first and second pneumatic actuators 24-1 and 24-2 expands, the other contracts. When the first pneumatic actuator 24-1 contracts and pulls the first power wire 21a, the second pneumatic actuator 24-2 expands and pushes the second power wire 21b. When the first pneumatic actuator 24-1 expands and pushes the first power wire 21a, the second pneumatic actuator 24-2 contracts and pulls the second power wire 21b.

As a result, the clutching unit 2 receives the pulling and pushing forces of the first and second power wires 21a and 21b through the joint 4, and oscillates in the direction of arrow B.

A driving source for displacing the clutching unit 2 is not limited to the first and second pneumatic actuators 24-1 and 24-2. Other driving sources using a hydraulic actuator or a motor may be used.

A joint holder side guide fixing part (first guide fixing part) 12a is provided in the joint side guide holder 12. The first guide fixing part 12a fixes the distal end of the sensing guide tube 32 to the joint-side guide holder 12. The first guide fixing part 12a fixes the sensing guide tube 32 by tightening a screw through a pressure plate. Or, the first guide fixing part 12a fixes the sensing guide tube 32 to the joint-side guide holder 12 by bonding.

The sensor holder 14 is provided with a sensor holder side guide fixing part (second guide fixing part). The second guide fixing part 14a fixes the rear end of the sensing guide tube 32 to the sensor holder 14. The second guide fixing part 14a fixes the sensing guide tube 32 to the sensor holder 14 by tightening a screw through a pressure plate. Or, the second guide fixing part 14a fixes the sensing guide tube 32 to the sensor holder 14 by bonding.

One end of the sensing guide tube 32 is fixed to the first guide fixing part 12a of the joint-side guide holder 12, and the other end is fixed to the second guide fixing part 14a of the sensor holder 14.

The sensor holder 14 is provided with a noncontact sensor 40. The noncontact sensor 40 is fixed to the sensor holder 14 by the sensor fixing part 14b. The sensor fixing part 14b fixes the noncontact sensor 40 to the sensor holder 14 by tightening a screw through a pressure plate. Or, the sensor fixing part 14b fixes the noncontact sensor 40 to the sensor holder 14 by bonding.

The noncontact sensor 40 detects a moving distance of the sensing wire 30 in the proximal end portion Q of the manipulator 1. The noncontact sensor 40 is a magnetic sensor, for example, and is called a magnetic sensor 40 hereinafter. As the magnetic sensor 40 is used, the sensing wire 30 is made of magnetic material such as SUS.

The sensor holder 14 is provided with a second wire exposed part 41. In the second wire exposed part 41, the sensing wire 30 is exposed from the sensing guide tube 32. The magnetic sensor 40 is arranged to the wire exposed part 41.

The magnetic sensor 40 is provided with a tubular part 40a. The sensing wire 30 is movably inserted in the tubular part 40a. In the tubular part 40a, the sensing wire 30 is moved along its own axis (linearly in the direction of arrow E and the reverse direction). When the sensing wire 30 is moved (displaced) in the tubular part 40a, the value of reactance generated between the tubular part 40a and sensing wire 30 is changed. The magnetic sensor 40 outputs a moving distance signal of the sensing wire 30 corresponding to the reactance value.

If the clutching unit 2 has three degrees of freedom, six magnetic sensors 40 are provided corresponding to six sensing wires 30. Therefore, displacement in each degree of freedom of the clutching unit 2 is detected based on a moving distance of each sensing wire detected by each magnetic sensor 40. Displacement in three degrees of freedom consists of displacement in rotation of the clutching unit 2 in the direction of arrow A about the central axis of the manipulator 1, displacement in oscillation of the clutching unit 2 in the direction of arrow B about the axis 3, and displacement in clutching by the clutching unit 2 in the direction of arrow C.

Next, an explanation will be given of detection of the degree of displacement of the clutching unit 2 in the apparatus configured as described above.

The first pneumatic regulator 25-1 controls the pneumatic pressure of the first pneumatic actuator 24-1. The second pneumatic regulator 25-2 controls the pneumatic pressure of the second pneumatic actuator 24-2. When the first pneumatic actuator 24-1 contracts and pulls the first power wire 21a, the second pneumatic actuator 24-2 expands and pushes the second power wire 21b. When the first pneumatic actuator 24-1 expands and pushes the first power wire 21a, the second pneumatic actuator 24-2 contracts and pulls the second power wire 21b. The force of pulling the first power wire 21a and force of pushing the second power wire 21b, or the force of pushing the first power wire 21a and force of pulling the second power wire 21b, are transmitted to the clutching unit 2 though the joint 4.

As a result, the clutching unit 2 receives the pulling and pushing forces of the first and second power wires 21a and 21b through the joint 4, and oscillates in the direction of arrow B. If the clutching unit 2 has three degrees of freedom, the clutching unit 2 rotates the manipulator 1 in the direction of arrow A about its own axis, and moves to effect clutching in the direction of arrow C, in addition to oscillating.

When the clutching unit 2 oscillates, the first pneumatic actuator 24-1 contracts, and the first power wire 21a moves in the axial direction indicated by arrow Da. As the sensing wire 30 is connected to the first power wire 21a, the sensing wire 30 moves in the axial direction indicated by arrow E in the sensing guide tube 32 corresponding to the moving distance of the first power wire 21a. As the friction between the sensing wire 30 and the inside wall of the sensing guide tube 32 is reduced, the sensing wire 30 moves in the sensing guide tube 32 without frictional resistance.

The moving distance of the sensing wire 30 is the same as that of the first power wire 21a. In other words, the sensing wire 30 moves in the sensing guide tube 32. One end of the sensing guide tube 32 is fixed to the first guide fixing part 12a, and the other end is fixed to the second guide fixing part 14a. Therefore, even if the first power wire 21a expands or sags, the length of the sensing guide tube 32 is unchanged. The moving distance of the first power wire 21a is the same as that of the sensing wire 30.

Therefore, the sensing wire 30 directly transmits a moving distance of the first power wire 21a to the magnetic sensor 40. In other words, a moving distance of the first power wire 21a corresponding to the displacement caused by oscillation of the clutching unit 2 is directly transmitted to the magnetic sensor as a moving distance of the sensing wire 30.

The magnetic sensor 40 detects a moving distance of the sensing wire 30 in the proximal end portion Q of the manipulator 1. When the sensing wire 30 is moved (displaced) in the tubular part 40a, the value of reactance generated between the tubular part 40a and sensing wire 30 is changed. The magnetic sensor 40 outputs a moving distance signal of the sensing wire 30 corresponding to the reactance value. According to the moving distance signal from the magnetic sensor 40, the displacement of the joint 4 caused by oscillation of the clutching unit is determined.

If the clutching unit 2 has three degrees of freedom, six sensing wires 30 are provided in the housing 10. Six magnetic sensors 40 are provided for six sensing wires 30. Displacement of the joint 4 in each degree of freedom of the clutching unit 2 is detected based on the moving distance signals from six magnetic sensors 40. Displacement of the joint 4 in three degrees of freedom consists of displacement in rotation of the clutching unit 2 in the direction of arrow A about its own axis, displacement in oscillation of the clutching unit 2 in the direction of arrow B about the axis 3, and displacement in clutching by the clutching unit 2 in the direction of arrow C.

As descried above, an embodiment of the invention comprises a sensing wire 30 which transmits a moving distance of a first power wire 21a; a sensing guide tube 32 which guides movement of the sensing wire 30; a magnetic sensor 40 which detects a moving distance of the sensing wire 30 in a proximal end portion Q of a manipulator 1; a joint holder 11 which holds a joint 4; a sensor holder 14 which holds a magnetic sensor 40; a joint-side guide holder 12 which fixes one end of the sensing guide tube 32; and a sensor holder side guide fixing part 14a which fixes the other end of the sensing guide tube 32. In this configuration, displacement of the joint 4 can be precisely detected in an area close to the joint 4 without increasing the diameter of the manipulator 1.

Since the sensing guide tube 32 is fixed to the first and second guide fixing parts 12a and 14a, even if the first power wire 21a expands or sags, the length of the sensing guide tube 32 is unchanged. As one of the sensing wire 30 is connected to the first power wire 21a in the area close to the joint 4, the sensing wire 30 is hardly affected by expansion or sag of the first power wire 21a.

Since the sensing wire 30 is connected to the first power wire 21a in the area close to the joint 4, and is not subjected to a stress for transmitting power, the sensing wire 30 is not affected by expansion or sag of the first power wire 21a.

Since the sensing wire 30 is not subjected to a stress for transmitting power, the sensing wire 30 may be made of a member having a diameter less than that of the first power wire 21a. The sensing wire 30 may be provided in a limited space having a diameter of less than 10 mm in the manipulator 1. The apparatus can precisely detect the degree of displacement of the joint 4 without increasing the diameter of the manipulator 1. The apparatus can detect a moving distance of the clutching unit 2 provided in the distal end portion P of the manipulator 1 more precisely than a conventional apparatus without increasing the diameter of the manipulator 1.

An electrical part such as a potentiometer and encoder is not used in proximity to the joint 4. The apparatus is hardly affected by heat and pressure, and detection of displacement of the joint 4 is not affected, even when the apparatus is sterilized.

Therefore, the apparatus can detect the degree of displacement of the joint 4 more precisely than is the case in an area close to a driving source comprising first and second pneumatic regulators 25-1 and 25-2 as in a conventional apparatus. The apparatus can precisely detect movement of the clutching unit 2 provided in the distal end portion P ahead of the joint 4.

Since the sensing wire 30 is formed smaller in diameter than the first power wire 21a, the sensing wire 30 can be provided in a limited space having a diameter of less than 10 mm in the housing 10. The apparatus can detect movement of the clutching unit 2 provided in the distal end portion P ahead of the joint 4 more precisely than a conventional apparatus without increasing the diameter of the manipulator 1.

Since the magnetic sensor 40 is of a noncontact type, it does not contact the sensing wire 30, and detects a moving distance of the sensing wire 30, without affecting movement of the sensing wire 30. The apparatus can precisely detect displacement of the joint 4 according to a moving distance of the sensing wire 30, and can detect movement of the clutching unit 2 more precisely.

The sensing wire 30 is guided throughout its length by the sensing guide tube 32 along the cylindrical housing 10. Therefore, the sensing wire 30 responds to displacement of the first power wire 21a, and moves by the same moving distance as that of the first power wire 21a. As a result, the apparatus can precisely detect displacement of the joint 4, and can detect movement of the clutching unit 2 more precisely.

The sensing guide tube 32 is formed tubular to insert the sensing wire 30. Since the sensing guide tube 32 guides the movement all around the sensing wire 30, the movement of the sensing wire 30 can be reliably guided.

The joint-side guide holder 12 comprises a power guide 23 to guide movement of the first power wire 21a, and a first fixing part 12a to fix the distal end of the sensing guide 32. This simplifies the configuration of the apparatus.

Between the connecting part 31 and joint-side first guide fixing part 12a, a joint-side exposed part is provided to expose the sensing wire 30 from the sensing guide tube 32. Even if a moving distance of the first power wire 21a is increased, the connecting part 31 does not interfere with the sensing guide tube 32. Movement of the first power wire 21a is precisely transmitted to the sensing wire 30.

The sensing guide tube 32 is provided in the housing 10 to movably guide the sensing wire 30. Therefore, the sensing wire 30 hardly sags, and the sensing wire 30 inserted into the sensing guide tube is placed in the housing in parallel with the first power wire 21a. A movement course of the first power wire 21a and sensing wire 30 are placed close to each other. As a result, the sensing wire 30 can precisely transmit the displacement of the joint 4 to the magnetic sensor 40.

In the housing 10, the joint-side guide holder 12 and at least a part of the proximal end portion Q of the manipulator 1, for example, the cylindrical unit 13, are made of flexible or semi-flexible material. Therefore, displacement of the joint 4 is detected in the joint 4 rather than in the first guide fixing part 12a. Even if at least a part of the proximal end portion Q of the manipulator 1 behind the first guide fixing part 12a is flexible or semi-flexible, displacement of the joint 4 can be detected. Movement of the clutching unit 2 can be precisely detected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

In the embodiment described above, the actuating unit is the clutching unit 2, such as a pair of forceps. The actuating unit may be anything that can be operated by the joint 4, for example, a surgical instrument such as a pair of scissors or a surgical knife.

In the embodiment described above, the entire length of the housing 10 and sensing guide tube 32 are made of hard material, such as SUS. The rear end side of the joint-side guide holder 12 may be made of flexible or semi-flexible material. In this case, as the displacement of the joint 4 is detected in a part close to the joint 4 ahead of the joint-side guide holder 12, movement of the clutching unit 2 can be precisely detected. Even if the sensing guide tube 32 is made of SUS, it can be bent by making the wall thickness 0.1 mm. Therefore, even if the housing 10 is made of flexible or semi-flexible material, displacement of the joint 4 can be detected.

Connection between the first power wire 21*a* and sensing wire 30 is completed by connecting the first power wire 21*a* to one end of the sensing wire 30, inserting the connected first power wire 21*a* into the power guide 23 of the joint-side guide holder 12, and inserting the sensing wire 30 into the sensing wire guide tube 32 fixed to the joint-side first guide fixing part 12*a* of the joint-side guide holder 12. Therefore, the housing 10 may be configured as one unit with the joint holder 11, the joint-side guide holder 12, and the cylindrical unit 13.

In the above embodiment, a tubular member is used for the sensing guide tube 32, which slidably guides the sensing wire 30 along movement of the first power wire 21*a*. The sensing guide tube 32 may be a guide member having an arc-shaped cross section, for example. In this case, a sensing guide tube is fixed by bonding, not by using a screw.

In the above embodiment, a fixing part of the sensing guide tube 32, which guides the first power wire 21*a*, and the power guide 23, are provided in the joint-side guide holder 12 that is one of the constituent elements. The fixing part of the sensing guide tube 32 and the power guide 23 may be provided at different positions along the length of the housing 10.

In the above embodiment, a noncontact magnetic sensor 40 is used, but an optical sensor may be used. When an optical sensor is used, the sensing wire 30 is made of Ni—Ti, for example, a slit of desired length is provided in an end portion exposed from the sensing guide tube 32, an optical fiber is provided opposing the slit, and the light reflected from the optical fiber is detected, thereby detecting a moving distance of the sensing wire 30.

A contact-type sensor may be used. In this case, a linear member made of SUS is additionally fixed to the distal end of the sensing wire 30 made of Ni—Ti, and a conductive needle is brought into contact with the SUS linear member, and a potential difference caused by movement of the linear member is measured, thereby detecting a moving distance. Friction between the needle and linear member is preferably as small as possible.

In the above embodiment, the manipulator 1 has three degrees of freedom. A manipulator may have one degree of freedom. A driving source is not limited to a pneumatic actuator. A driving source may be a hydraulic or oil hydraulic actuator, or a motor.

What is claimed is:

1. A manipulator joint displacement detection mechanism comprising:
    a manipulator which includes an actuating unit and a joint, and is formed in an elongated shape having a distal end portion and a proximal end portion,
        the actuating unit provided in the distal end portion, and
        the joint configured to displace to perform an actuating operation to the actuating unit, and transmit the displacement to the actuating unit to perform the actuating operation;
    a first transmission member which is connected to the joint, and provided movably to displace the joint;
    a second transmission member which is connected to the first transmission member in a part of the manipulator close to the joint, and is moved corresponding to a moving distance of the first transmission member;
    a guide which guides the movement of the second transmission member, the guide comprising a first end and a second end;
    a sensor which detects the moving distance of the second transmission member in a part close to the proximal end portion of the manipulator;
    a joint holder which holds the joint;
    a sensor holder which holds the sensor;
    a first guide fixing part which is provided in the joint holder, and fixes the first end of the guide; and
    a second guide fixing part which is provided in the sensor holder, and fixes the second end of the guide.

2. The manipulator joint displacement detection mechanism according to claim 1, wherein the guide is formed in a tubular shape, in which the second transmission member is inserted.

3. The manipulator joint displacement detection mechanism according to claim 1, further comprising:
    a connecting part which connects the first and second transmission members,
    wherein the second transmission member has a first exposed part which is exposed from the guide between the connecting part and the first guide fixing part.

4. The manipulator joint displacement detection mechanism according to claim 1, further comprising:
    a cylindrical housing which is provided between the first guide fixing part and the second guide fixing part,
    wherein the housing houses at least the first transmission member, the guide, and the second transmission member.

5. The manipulator joint displacement detection mechanism according to claim 4, wherein the housing and the guide are made of flexible or semi-flexible member in a part between the first guide fixing part and the proximal end portion of the manipulator.

6. The manipulator joint displacement detection mechanism according to claim 1, wherein the sensor includes a noncontact sensor.

7. The manipulator joint displacement detection mechanism according to claim 6, wherein the sensor includes a magnetic sensor.

8. The manipulator joint displacement detection mechanism according to claim 1,
    wherein the second transmission member has a second exposed part which is exposed from the guide within the sensor holder, and
    the sensor is provided in the second exposed part.

9. The manipulator joint displacement detection mechanism according to claim 1, wherein the second transmission member is formed to be thinner than the first transmission member.

10. The manipulator joint displacement detection mechanism according to claim 9, wherein the second transmission member is formed in a linear shape.

11. The manipulator joint displacement detection mechanism according to claim 1,
    wherein the first transmission member includes a first wire, the second transmission member includes a second wire, and the diameter of the second wire is less than the diameter of the first wire.

12. The manipulator joint displacement detection mechanism according to claim 1, wherein the second wire moves the same moving distance as the moving distance of the first wire.

13. A manipulator joint displacement detection mechanism comprising:
- a manipulator which includes a actuating unit and a joint, and is formed in an elongate shape having a distal end portion and a proximal end portion,
  the actuating unit provided in the distal end portion, and the joint configured to displace to perform an actuating operation to the actuating unit, and transmit the displacement to the actuating unit to perform the actuating operation;
- a first transmission member which is connected to the joint, and provided movably to displace the joint;
- a second transmission member which moves corresponding to movement of the first transmission member;
- a guide which guides movement of the second transmission member, the guide comprising a first end and a second end;
- a guide fixing part which fixes the first end and the second end of the guide; and
- a sensor which detects a moving distance of the second transmission member in the proximal end portion of the manipulator.

14. The manipulator joint displacement detection mechanism according to claim 13, wherein the guide is formed in a tubular shape, in which the second transmission member is inserted.

15. The manipulator joint displacement detection mechanism according to claim 13, wherein the sensor includes a noncontact sensor.

16. The manipulator joint displacement detection mechanism according to claim 15, wherein the sensor includes a magnetic sensor.

17. The manipulator joint displacement detection mechanism according to claim 13, wherein the second transmission member is formed to be thinner than the first transmission member.

18. The manipulator joint displacement detection mechanism according to claim 17, wherein the second transmission member is formed in a linear shape.

19. The manipulator joint displacement detection mechanism according to claim 13,
wherein the first transmission member includes a first wire, the second transmission member includes a second wire, and
the diameter of the second wire is less than the diameter of the first wire.

20. The manipulator joint displacement detection mechanism according to claim 19, wherein the second wire moves the same moving distance as the moving distance of the first wire.

* * * * *